United States Patent
Kurihara et al.

(10) Patent No.: US 10,413,641 B2
(45) Date of Patent: Sep. 17, 2019

(54) SUCTION DEVICE

(71) Applicant: Murata Manufacturing Co., Ltd., Kyoto (JP)

(72) Inventors: Kiyoshi Kurihara, Kyoto (JP); Daisuke Kondo, Kyoto (JP); Hiroshi Takemura, Kyoto (JP); Yoshinori Ando, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 554 days.

(21) Appl. No.: 15/167,092

(22) Filed: May 27, 2016

(65) Prior Publication Data

US 2016/0271305 A1    Sep. 22, 2016

Related U.S. Application Data

(63) Continuation of application No. PCT/JP2015/052441, filed on Jan. 29, 2015.

(30) Foreign Application Priority Data

Jan. 30, 2014  (JP) ................................. 2014-015088
Apr. 30, 2014  (JP) ................................. 2014-094272
Aug. 19, 2014  (JP) ................................. 2014-166607

(51) Int. Cl.
*A61M 1/00*    (2006.01)
*A61M 1/06*    (2006.01)

(52) U.S. Cl.
CPC .......... *A61M 1/0023* (2013.01); *A61M 1/009* (2014.02); *A61M 1/0011* (2013.01);
(Continued)

(58) Field of Classification Search
CPC .............. A61M 1/0011; A61M 1/0019; A61M 1/0023; A61M 1/0025; A61M 1/0031;
(Continued)

(56) References Cited

U.S. PATENT DOCUMENTS 3,369,348 A * 2/1968 Davis .................... B01D 46/02
                                                              248/95
3,957,051 A    5/1976 Topham
(Continued)

FOREIGN PATENT DOCUMENTS

EP    2 436 291 A1    4/2012
GB    1 400 139 A     7/1975
(Continued)

OTHER PUBLICATIONS

EP Office Action for EP Application No. 15743244.4 dated Dec. 22, 2017.
(Continued)

*Primary Examiner* — Adam Marcetich
(74) *Attorney, Agent, or Firm* — Pearne & Gordon LLP

(57) ABSTRACT

Provided is a suction device that can suppress sound and vibration during use. A suction device includes a flow-passage forming section (1) having a suction port (20) from which fluid is sucked, a discharge port (29) from which the fluid is discharged, and a flow passage (2) which is sealed from an outside except at the suction port (20) and the discharge port (29) and through which the fluid flows, and a piezoelectric driving part (33) that generates a flow of the fluid in the flow passage (2). The piezoelectric driving part (33) includes a diaphragm (37) and a piezoelectric element (34) as a moving part that transmits driving force to the fluid. The moving part is entirely disposed inside the flow passage (2).

19 Claims, 10 Drawing Sheets

(52) U.S. Cl.
CPC ........ *A61M 1/0019* (2013.01); *A61M 1/0025* (2014.02); *A61M 1/0031* (2013.01); *A61M 1/0056* (2013.01); *A61M 1/0066* (2013.01); *A61M 1/0088* (2013.01); *A61M 1/06* (2013.01); *A61M 1/0052* (2014.02); *A61M 1/062* (2014.02); *A61M 2205/42* (2013.01); *A61M 2205/8206* (2013.01); *A61M 2210/0618* (2013.01)

(58) Field of Classification Search
CPC .............. A61M 1/0052; A61M 1/0056; A61M 1/0066; A61M 1/0088; A61M 1/009; A61M 1/06; A61M 1/062; A61M 2205/42; A61M 2205/8206; A61M 2210/0618; A61M 1/0064; A61M 2205/0294; F04B 43/046; F04B 19/006; F04B 43/04; F04B 45/047; A61B 2017/246; A61B 17/24
See application file for complete search history.

(56) References Cited

U.S. PATENT DOCUMENTS

| | | | | |
|---|---|---|---|---|
| 5,052,147 | A * | 10/1991 | Broomfield | A01M 1/06 43/139 |
| 5,876,387 | A | 3/1999 | Killian et al. | |
| 6,059,803 | A * | 5/2000 | Spilman | A61M 1/0023 604/319 |
| 6,135,980 | A * | 10/2000 | Vu | A61M 1/0003 604/315 |
| 6,471,679 | B1 | 10/2002 | Suh | |
| 6,676,644 | B2 | 1/2004 | Ikeda | |
| 2002/0198488 | A1* | 12/2002 | Yao | A61M 1/0049 604/35 |
| 2003/0101523 | A1* | 6/2003 | Lepley, Jr. | E04H 4/1636 15/1.7 |
| 2003/0163101 | A1* | 8/2003 | Say | A61M 1/0003 604/319 |
| 2004/0040901 | A1* | 3/2004 | Page | B01D 17/00 210/163 |
| 2004/0105769 | A1 | 6/2004 | Wu et al. | |
| 2005/0120511 | A1* | 6/2005 | Pedersen | A45D 24/32 15/402 |
| 2008/0082059 | A1 | 4/2008 | Fink et al. | |
| 2008/0312674 | A1* | 12/2008 | Chen | A61M 1/0058 606/162 |
| 2009/0048581 | A1* | 2/2009 | Sebban | A61M 1/0003 604/540 |
| 2009/0167109 | A1 | 7/2009 | Tomita | |
| 2010/0042059 | A1 | 2/2010 | Pratt | |
| 2010/0049150 | A1 | 2/2010 | Braga et al. | |
| 2011/0076170 | A1* | 3/2011 | Fujisaki | F04B 45/047 417/415 |
| 2011/0184341 | A1 | 7/2011 | Baker et al. | |
| 2012/0016323 | A1 | 1/2012 | Robinson et al. | |
| 2012/0046625 | A1 | 2/2012 | Johannison | |
| 2012/0316538 | A1 | 12/2012 | Heiser et al. | |
| 2013/0266461 | A1 | 10/2013 | Hirata et al. | |
| 2014/0107599 | A1 | 4/2014 | Fink et al. | |
| 2014/0305436 | A1 | 10/2014 | Nitta | |

FOREIGN PATENT DOCUMENTS

| | | |
|---|---|---|
| JP | S49-58686 A | 6/1974 |
| JP | H09-509866 A | 10/1997 |
| JP | 2001-218831 A | 8/2001 |
| JP | 2009-156182 A | 7/2009 |
| JP | 2010-000159 A | 1/2010 |
| JP | 2010-527636 A | 8/2010 |
| JP | 2011-530350 A | 12/2011 |
| JP | 2012-500086 A | 1/2012 |
| JP | 4934751 B1 | 5/2012 |
| JP | 2012-525202 A | 10/2012 |
| JP | 2013-538071 A | 10/2013 |
| JP | 2013-255824 A | 12/2013 |
| WO | 2010/032607 A1 | 3/2010 |
| WO | 2010/137191 A1 | 12/2010 |
| WO | 2011/130570 A1 | 10/2011 |
| WO | 2013/084918 A1 | 6/2013 |
| WO | 2015098779 A1 | 7/2015 |

OTHER PUBLICATIONS

International Search report for PCT/JP2015/052441 dated Apr. 7, 2015.
Written Opinion or PCT/JP2015/052441 dated Apr. 7, 2015.
Supplementary European Search Report issued in EP15743244.4 dated Mar. 30, 2017.
Office action issued in JP2015-559999.

* cited by examiner

SUCTION DEVICE

FIELD OF THE DISCLOSURE

The present invention relates to a suction device used to remove a collection object such as nasal mucus.

DESCRIPTION OF THE RELATED ART

For example, cold, nasal inflammation, and empyema cause a symptom, such as nasal congestion, due to excessive secretion of nasal mucus. Although nasal congestion is generally removed by nose blowing, for example, nasal mucus of infants who cannot blow their noses needs to be removed by a helper. At this time, a small amount of nasal mucus can be removed with a tissue or a cotton swab, but it is difficult to remove a large amount of nasal mucus.

Accordingly, electric suction devices capable of easily removing a large amount of nasal mucus have recently been popularized (see, for example, Patent Documents 1 and 2). FIG. 11A is a cross-sectional view of a suction device 201 of the related art referring to Patent Document 1. FIG. 11B is an exploded perspective view illustrating the principal part of the suction device 201.

The suction device 201 includes a case 202, a nasal mucus storage cylinder 203, and a nasal mucus suction port 204. The nasal mucus suction port 204 is a portion to be inserted in the nasal cavity, and is shaped like a cylinder. The nasal mucus storage cylinder 203 is provided between the nasal mucus suction port 204 and the case 202, and has an internal space that stores liquid sucked from the nasal mucus suction port 204. The case 202 serves as a grip portion of the suction device 201, and has a power switch 205 on a part of its surface. The case 202 includes therein a battery 206, a motor 207, an eccentric cam 208, and a vacuum generating means (pump) 209. The power switch 205 switches between on and off states of driving of the motor 207. The motor 207 is driven by power supplied from the battery 206 to turn the eccentric cam 208. The pump 209 includes a pump body 210, a valve 211, and opening and closing plates (valve members) 212 and 213. The valve 211 and the valve members 212 and 213 are attached to block up the pump body 210. The eccentric cam 208 moves the valve 211 up and down relative to the pump body 210. Thus, the capacity changes inside the pump body 210, and the air pressure changes inside the pump body 210. The valve member 212 is provided in a suction passage communicating with the nasal mucus storage cylinder 203, and is structured to suck fluid into the pump body 210. The valve member 213 is provided in a discharge passage communicating with the external space, and is structured to discharges fluid from the pump body 210.

There exists a therapy called a negative pressure wound therapy for promoting the recovery of a wound site by applying a negative pressure to a surface of the wound site in the treatment of an injury or the like. For example, Patent Document 3 discloses a suction device that includes a wound dressing to be in close contact with the outer periphery of a wound site and removes an exudate from the wound site.

Patent Document 1: Japanese Unexamined Patent Application Publication No. 2001-218831

Patent Document 2: Japanese Unexamined Patent Application Publication (Translation of PCT Application) No. 2010-527636

Patent Document 3: Japanese Unexamined Patent Application Publication No. 2013-255824

BRIEF SUMMARY OF THE DISCLOSURE

The suction device of the related art sometimes has a problem in that the motor sound and the vibration caused during the use are large. For example, in the case of a suction device for sucking nasal mucus, an infant moves his or her body in response to the motor sound and the vibration, and this sometimes makes it difficult to perform the operation of sucking the nasal mucus. In the case of a suction device for the negative pressure wound therapy, since the device needs to be continuously driven for a long time, the patient may experience discomfort from the motor sound and the vibration. Particularly when the suction device is worn in contact with the affected part or skin, the patient may experience significant discomfort from the vibration.

Accordingly, an object of the present invention is to provide a suction device that can suppress sound and vibration during use.

A suction device according to the present invention includes a flow-passage forming section having a suction port from which fluid is sucked, a discharge port from which the fluid is discharged, and a flow passage which is sealed from an outside except at the suction port and the discharge port and through which the fluid flows, and a driving part that generates a flow of the fluid in the flow passage. In the driving part, a moving part that transmits the driving force to the fluid is entirely disposed inside the flow passage. In particular, the driving part is preferably driven to make a fluid pressure in the flow passage on a side of the suction port a negative pressure relative to a fluid pressure outside the flow passage and to make a fluid pressure in the flow passage on a side of the discharge port a positive pressure relative to the fluid pressure outside the flow passage.

According to these structures, the leakage of the driving sound and vibration from the flow passage can be suppressed by disposing the driving part in the sealed flow passage. Portions of the driving part other than the moving part may be provided separately from the flow-passage forming section or may be provided integrally therewith. When the portions are integrally provided, the noise can be even further reduced because since portions connected between the members are reduced in the whole suction device.

Preferably, the flow-passage forming section further includes a pump chamber whose inner capacity is changed by the movement of the moving part in the flow-passage forming section, and the pump chamber constantly communicates with the outside via the flow passage.

According to this structure, a complicated mechanism, such as a valve or a valve part for opening and closing the pump chamber is unnecessary, and this can simplify the configuration of the suction device. Further, since the pressure in the pump chamber is quickly released to the atmospheric pressure via the flow passage when the driving part stops the operation, the nasal cavity or the like does not continue to adhere after the driving part stops the operation. For this reason, an operation of releasing the pressure when the operation of the driving part is stopped is unnecessary, and the suction device easily separates from the skin and has high responsiveness. In this regard, discomfort is also unlikely to be experienced by the user.

Preferably, the moving part includes a piezoelectric member that deforms by the application of a driving voltage and an elastic member to which the piezoelectric member is attached.

According to this structure, sliding does not occur in the driving part unlike a motor, and the driving sound and vibration caused in the driving part can be suppressed further.

Preferably, a total cross-sectional area of the flow passage on a discharge side is smaller than a total cross-sectional area on a suction side.

According to this structure, the driving sound and vibration leaking from the discharge side of the flow-passage forming section can be suppressed.

Preferably, a flowing direction of the fluid sucked by the driving part is substantially the same as a flowing direction of the fluid discharged by the driving part.

According to this structure, the path length of the fluid on the discharge side can be shortened (or the path length can be made about zero), and the pressure loss of the fluid caused in the path of the fluid can be suppressed. This can increase the flow rate and flow velocity of the fluid flowing from the outside and reduce the size of the device. Further, since the path of the fluid before and after the driving part is a buffer against the fluid, if the path length of the fluid is long, the time required from when the driving part starts driving to when the pressure of the fluid reaches a predetermined pressure increases. In this structure, however, since the path length of the fluid can be shortened, the buffer can be reduced. This can configure a highly responsive suction device such that the time required from when a driving part starts driving to when the pressure of fluid reaches a predetermined pressure is short.

Preferably, the suction device further includes a filter that blocks a collection object contained in the fluid.

According to this structure, the collection object contained in the fluid can be prevented from reaching the driving part, and this allows the driving part to be driven stably. Further, the filter can suppress the leakage of the driving sound and vibration from the suction side of the flow-passage forming section.

The suction device may further include a housing having an internal space that houses a rear end portion of the flow-passage forming section with the discharge port in a state in which a front end portion of the flow-passage forming section with the suction port is exposed outside, and an air vent communicating with the internal space.

According to this structure, it is possible to configure a portable suction device that can perform an operation of sucking nasal mucus and the like and to suppress the leakage of the driving sound and vibration from the discharge side of the flow-passage forming section by the housing. The housing and the flow-passage forming section may be separately provided or may be integrally provided. When the housing and the flow-passage forming section are integrally provided, the noise can also be even further reduced because portions connected between the members are reduced in the whole suction device.

Preferably, the flow-passage forming section further includes a storage unit provided on an upstream side of the driving part in the flow passage in a flow of the fluid to store a collection object contained in the fluid.

According to this structure, the collection object can be handled easily. The storage unit may be provided separately from other portions that constitute the flow-passage forming section, or may be provided integrally therewith. When the housing is provided integrally with the other portions that constitute the flow-passage forming section, the noise can also be even further reduced because portions connected between the members are reduced in the whole suction device.

The suction device may further include a protective film having an aperture communicating with the suction port and provided to be adhered to a wound site.

According to this structure, the suction device can be used for a negative pressure wound therapy. Since the driving sound and vibration are suppressed in the suction device, the discomfort of the patient who receives the negative pressure wound therapy can be suppressed, and the suction device can be easily worn in contact with the affected part or skin.

Preferably, the storage unit is a bag-shaped inner canister including a bag mouth portion communicating with the suction port and an expandable and contractable expanding and contracting portion having an internal space sealed except at the bag mouth portion.

According to this structure, the fluid sucked from the suction port can be prevented from directly flowing into the flow passage. Further, the inner canister can suppress the leakage of the driving sound and vibration from the flow-passage forming section. The inner canister and the flow-passage forming section may be separately provided, or may be integrally provided. When the inner canister and the flow-passage forming section are integrally provided, the noise can also be even further reduced because the portions connected between the members are reduced in the whole suction device.

Preferably, the bag mouth portion is detachable from the suction port.

According to this structure, the fluid sucked from the outside can be easily taken out of the suction device, and an operation of cleaning the flow passage is unnecessary.

Preferably, the bag mouth portion connects the expanding and contracting portion and the suction port in a sealed state. Preferably, the expanding and contracting portion further includes a fixing material that fixes liquid therein.

According to these structures, it is possible to more reliably prevent the leakage of the fluid from the inner canister.

Preferably, the fluid is gas.

According to this structure, since the sound caused in the driving part is likely to be transmitted via the gas, the propagation of the sound to the outside of the flow passage can be pronouncedly suppressed by the effect of blocking with the flow-passage forming section.

According to the present invention, it is possible to suppress the occurrence of the driving sound and vibration and to suppress the leakage of the occurring driving sound and vibration to the outside.

DETAILED DESCRIPTION OF THE DISCLOSURE

A plurality of embodiments of the present invention will be described below using some specific examples with reference to the drawings. Each of the embodiments is illustrative and the structures shown in different embodiments can be partially replaced and combined.

Hereinafter, the direction in which a suction device is directed toward, for example, an affected part to be subjected to a suction operation during use is referred to as a frontward direction, and the direction in which fluid is sucked is referred to as a rearward direction.

Figure 1A:
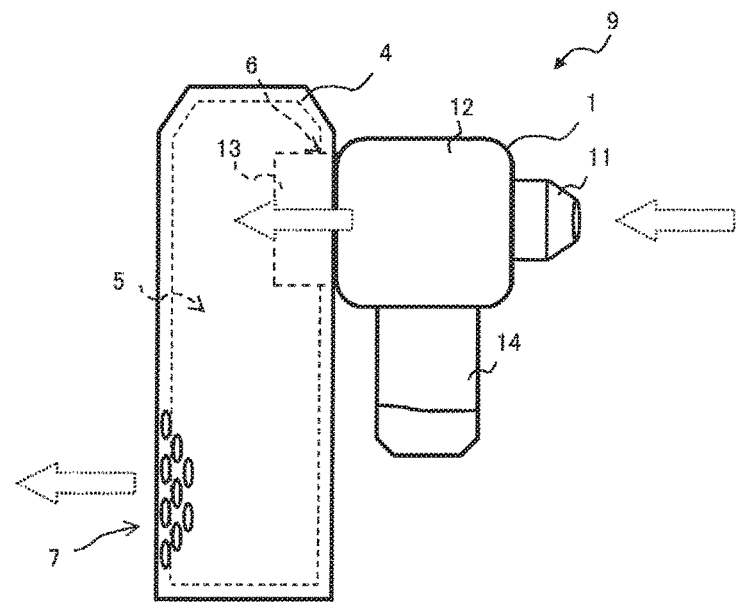
FIGS. 1A and 1B include side views of a suction device according to a first embodiment and a sectional side view of the principal part thereof.

FIG. 1A is a side view of a suction device 9 according to a first embodiment of the present invention.

Here, the suction device 9 is a liquid suction device for nasal mucus and the like, and includes a flow-passage forming section 1 and a housing 4. The flow-passage forming section 1 is disposed at a front end of the suction device 9, and is directed toward the affected part or the like during use. The housing 4 is disposed at a rear end of the suction device 9, and is gripped by an operator or the like during use.

The flow-passage forming section 1 includes a nozzle 11, a separator 12, a driving unit 13, and a storage unit 14. The nozzle 11, the separator 12, the driving unit 13, and the storage unit 14 are separably provided so that each of them can be cleaned easily. In the connecting portions among the nozzle 11, the separator 12, the driving unit 13, and the storage unit 14, unillustrated packing materials or the like are provided to hermetically seal the connecting portions. The nozzle 11, the separator 12, the driving unit 13, and the storage unit 14 may be appropriately combined.

The housing 4 is a cylindrical member having closed upper and lower ends. Inside the housing 4, an internal space 5 is provided to house unillustrated components such as a battery and a power feeding circuit. A front side of an outer surface of the housing 4 has a connecting port 6 communicating with the internal space 5. A rear side of the outer surface of the housing 4 has a plurality of air vents 7 communicating with the internal space 5. A rear end of the flow-passage forming section 1 is inserted in the connecting port 6, and this connects the flow-passage forming section 1 and the housing 4. An unillustrated packing material or the like is provided in the connecting portion between the flow-passage forming section 1 and the housing 4, and this hermetically seals the connecting portion. The flow-passage forming section 1 and the housing 4 may be integrally provided. In this case, the noise can be further reduced because portions connected between the members are reduced in the whole suction device.

The above-described components roughly operate as follows. The nozzle 11 is used while being inserted into a nasal cavity of a patient or the like, and sucks fluid such as nasal mucus. The separator 12 separates a collection object, such as nasal mucus, and the gas contained in the fluid sucked by the nozzle 11. The storage unit 14 stores the collection object separated by the separator 12. The driving unit 13 sucks the gas separated by the separator 12 and discharges the gas into the internal space 5 of the housing 4. The internal space 5 of the housing 4 communicates with an external space of the housing 4 through the plural air vents 7 so that the pressure in the internal space 5 is kept substantially equal to the air pressure in the external space. For this reason, the gas discharged by the driving unit 13 diffuses in the internal space 5 of the housing 4, and the pressure and flow velocity thereof decrease.

To suppress the leakage of the driving sound and vibration caused in the driving unit 13 of the flow-passage forming section 1 to the outside, the plural air vents 7 are preferably provided near a lower end of the housing 4 far from the driving unit 13 disposed near an upper end of the housing 4.

Figure 1B:
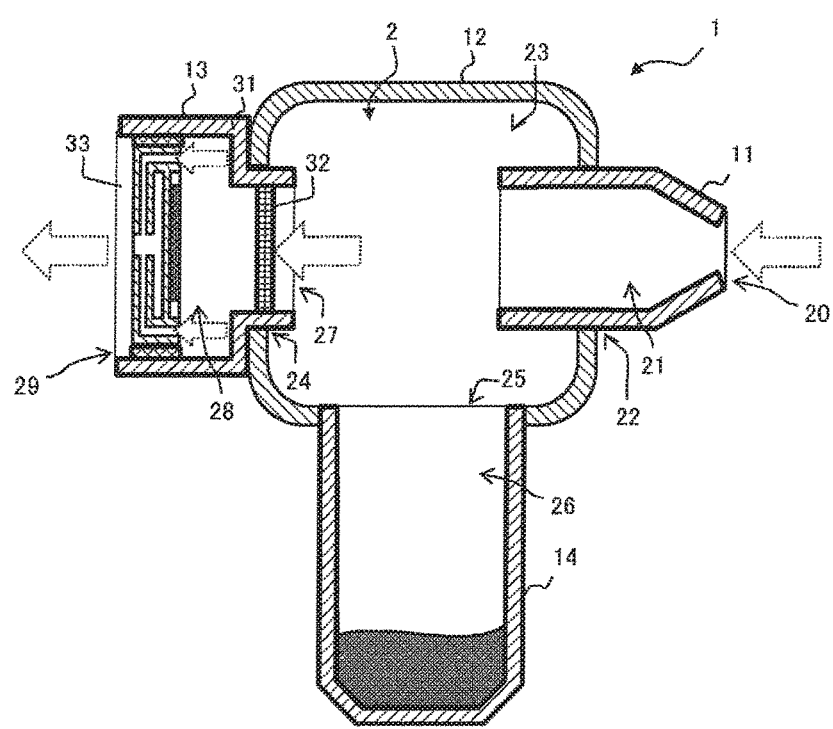

FIG. 1B is a sectional side view of the flow-passage forming section 1. A flow passage 2 is provided inside the flow-passage forming section 1. The flow passage 2 connects an upper chamber 23 provided in the separator 12, a lower chamber 26 provided inside the storage unit 14, a flow passage 21 provided inside the nozzle 11, and a flow passage 28 provided inside the driving unit 13 in a manner such that they communicate with one another in a sealed state.

The nozzle 11 is a cylindrical member inclined so that its outer shape narrows toward a front end. The front end of the nozzle 11 has a suction port 20 from which an external fluid containing nasal mucus and the like is sucked. Inside the nozzle 11, the flow passage 21 is provided to communicate with the suction port 20. The external fluid containing nasal mucus and the like is sucked from the suction port 20 into the separator 12 through the flow passage 21. The nozzle 11 may be separable from other portions that constitute the flow-passage forming section 1, or may be provided integrally with the other portions that constitute the flow-passage forming section 1. When the nozzle 11 is provided integrally with the flow-passage forming section 1, the noise can be even further reduced because the portions connected between the members are reduced in the whole suction device.

The separator 12 is a box-shaped member. A front surface of the separator 12 has an opening 22 in which a rear end of the nozzle 11 is inserted. A rear surface of the separator 12 has an opening 24 in which a front end of the driving unit 13 is inserted. A lower surface of the separator 12 has an opening 25 in which an upper end of the storage unit 14 is inserted. Inside the separator 12, the upper chamber 23 is provided to communicate with the opening 22, the opening 24, and the opening 25. In the upper chamber 23, the rear end of the nozzle 11 and the front end of the driving unit 13 are disposed opposed to each other with a predetermined distance therebetween. The external fluid containing nasal mucus and the like is sucked from the flow passage 21 of the nozzle 11 to the upper chamber 23, and drops downward inside the upper chamber 23. Thus, liquid, such as nasal mucus, and gas contained in the fluid sucked by the separator 12 are separated. The separator 12 may also be separable from other portions that constitute the flow-passage forming section 1, or may be provided integrally therewith. When the separator 12 is provided integrally with the flow-passage forming section 1, the noise can be even further reduced because the portions connected between the members are reduced in the whole suction device.

The storage unit 14 is a cylindrical member. Inside the storage unit 14, the lower chamber 26 is provided. The lower chamber 26 is open at the upper end of the storage unit 14, and stores liquid, such as nasal mucus, separated and dropped by the separator 12. The storage unit 14 may also be separable from other portions that constitute the flow-passage forming section 1, and may be provided integrally therewith. When the storage unit 14 is provided integrally with the flow-passage forming section 1, the noise can also be even further reduced because the portions connected between the members are reduced in the whole suction device.

The driving unit 13 includes a cylindrical body 31, a filter 32, and a piezoelectric driving part 33. The cylindrical body 31 is a cylindrical member. A front end of the cylindrical body 31 has an internal suction port 27 from which the gas separated by the separator 12 is sucked. A rear end of the cylindrical body 31 has a discharge port 29 from which the gas sucked from the internal suction port 27 is discharged. Inside the cylindrical body 31, the flow passage 28 is provided to communicate with the internal suction port 27 and the discharge port 29. The filter 32 and the piezoelectric driving part 33 are housed in the flow passage 28 to block up the flow passage 28. The filter 32 is a membrane formed by nonwoven paper or sponge and provided on a front side of the piezoelectric driving part 33, and prevents liquid, such as nasal mucus, from flowing into the piezoelectric driving part 33. The cylindrical body 31 may also be separable from other portions that constitute the flow-passage forming section 1, or may be provided integrally therewith. When the cylindrical body 31 is provided integrally with the flow-passage forming section 1, the noise can also be even further reduced because the portions connected between the members are reduced in the whole suction device.

The flow-passage forming section 1 has the above-described configuration.

Next, the piezoelectric driving part 33 will be described more specifically. The piezoelectric driving part 33 corresponds to the driving part described in the claims, and sucks the gas from the flow passage 28 and discharges the gas to the discharge port 29. Thus, the piezoelectric driving part 33 generates, inside of the flow-passage forming section 1 (flow passage 2), a flow of fluid directed from the suction port 20 to the discharge port 29 via the flow passage 21, the upper chamber 23, and the flow passage 28.

Figure 2:
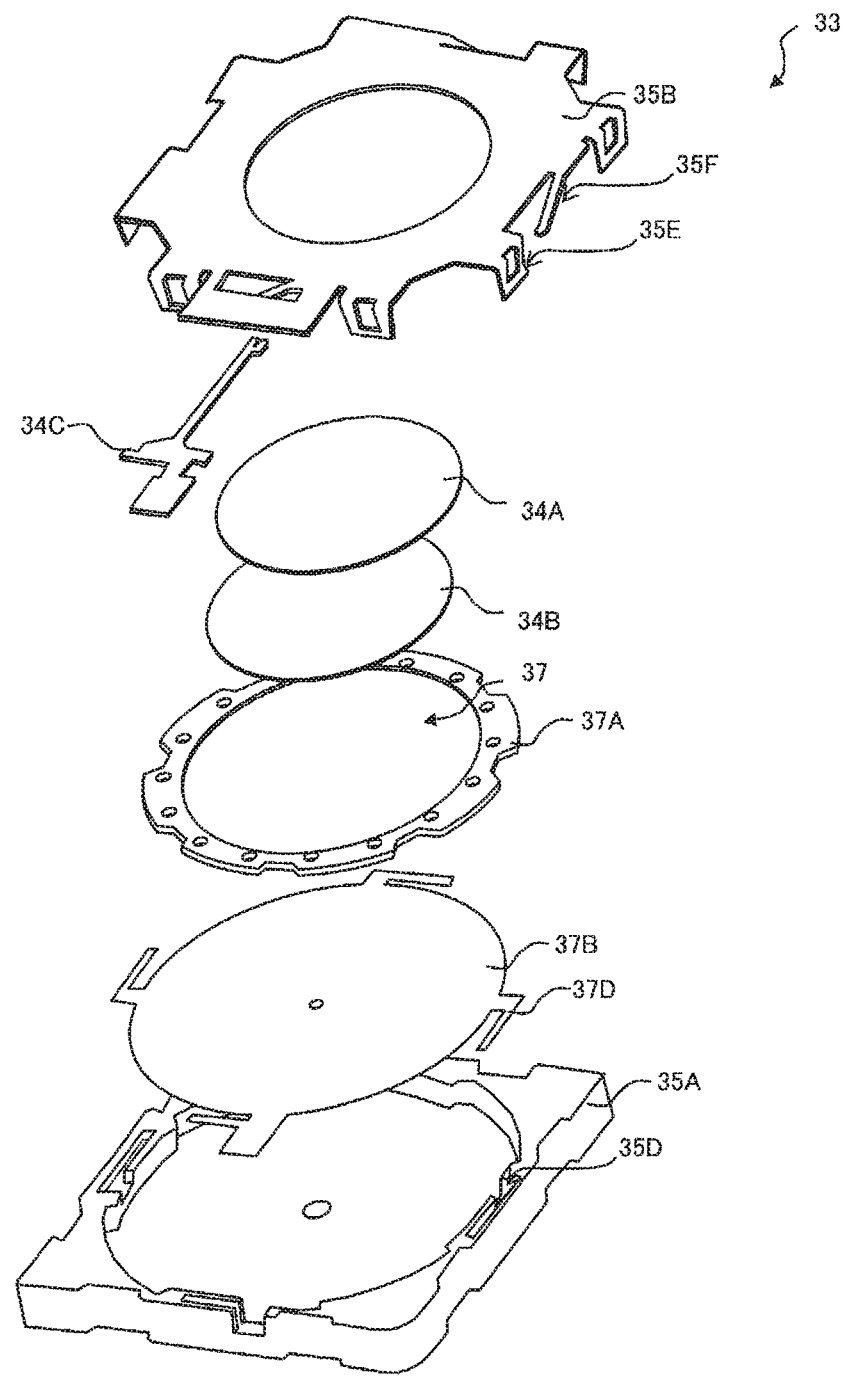
FIG. 2 is an exploded perspective view of a piezoelectric driving part in the suction device of the first embodiment.

FIG. 2 is an exploded perspective view of the piezoelectric driving part 33.

The piezoelectric driving part 33 includes a piezoelectric element 34A, a reinforcing plate 34B, a floating terminal 34C, a diaphragm forming plate 37A, an opposed plate 37B, a case portion 35A, and a cover portion 35B. The piezoelectric element 34A, the reinforcing plate 34B, the diaphragm forming plate 37A, and the opposed plate 37B are stacked and fixed while being held between the case portion 35A and the cover portion 35B. The piezoelectric driving part 33 is disposed in a manner such that an illustrated top side, that is, a side of the cover portion 35B faces the internal suction port 27 of the above-described cylindrical body 31 and a bottom side, that is, a side of the case portion 35A faces the discharge port 29 of the above-described cylindrical body 31.

The piezoelectric element 34A corresponds to the piezoelectric member described in the claims. The piezoelectric element 34A is disc-shaped, and has electrodes on both surfaces. The electrode provided on the bottom surface of the piezoelectric element 34A is connected to a reference potential via another member. To the electrode provided on the top surface of the piezoelectric element 34A, an alternating-current driving voltage is applied from a power feeding circuit (not illustrated) via the floating terminal 34C.

The reinforcing plate 34B has substantially the same outer shape as that of the piezoelectric element 34A, and is joined to the bottom surface of the piezoelectric element 34A. The reinforcing plate 34B is provided to suppress the deformation due to the difference in linear expansion coefficient between the piezoelectric element 34A and the diaphragm forming plate 37A, and is formed of a material having a linear expansion coefficient higher than those of both the piezoelectric element 34A and the diaphragm forming plate 37A (or a material having a linear expansion coefficient lower than those of both of them).

The diaphragm forming plate 37A is disc-shaped. A peripheral edge portion thereof is thick, and a center portion thereof is recessed from the peripheral edge portion on both surfaces. One principal surface of the peripheral edge portion of the diaphragm forming plate 37A is in contact with the cover portion 35B, and the other principal surface is in contact with the opposed plate 37B. The center portion of the diaphragm forming plate 37A forms a diaphragm 37, and is joined to the bottom surface of the piezoelectric element 34A with the reinforcing plate 34B being disposed therebetween. The diaphragm 37 corresponds to the elastic member described in the claims, which makes bending vibration along with the driving of the piezoelectric element 34A. Therefore, the diaphragm 37, the piezoelectric element 34A, and the reinforcing plate 34B constitute the moving part described in the claims.

The opposed plate 37B has a through hole in its center, and has a plurality of engaging pieces 37D projecting outward from its outer periphery. The opposed plate 37B substantially has the same size as that of the peripheral edge portion of the diaphragm forming plate 37A, is opposed to the center portion (diaphragm 37) of the diaphragm forming plate 37A with a distance therebetween, and is in contact with the peripheral edge portion of the diaphragm forming plate 37A. For this reason, a space serving as a pump chamber 42 to be described later is formed between the opposed plate 37B and the diaphragm 37.

The opposed plate 37B, the diaphragm forming plate 37A, and the reinforcing plate 34B are formed of a conductive material. One of the plural engaging pieces 37D projecting outward from the outer periphery of the opposed plate 37B also functions as a terminal for connecting the electrode on the other principal surface of the piezoelectric element 34A to the reference potential.

The case portion 35A is shaped like a box having an internal space that houses the piezoelectric element 34A, the reinforcing plate 34B, the floating terminal 34C, the diaphragm forming plate 37A, and the opposed plate 37B, has a through hole serving as a discharge-side flow passage 43 to be described later in the center of an inner bottom surface, and has engaging grooves 35D for engaging with the plural engaging pieces 37D of the opposed plate 37B in an inner side wall portion. The depth of the engaging grooves 35D is less than the thickness of the side wall portion of the case portion. Thus, a space serving as a connecting chamber 44 to be described later is formed between the inner bottom surface of the case portion 35A and the opposed plate 37B.

The cover portion 35B is shaped like a lid covering the case portion 35A, and includes engaging claws 35E to be engaged with the outer side surface of the case portion 35A and elastic pieces 35F for pressing the engaging pieces 37D of the opposed plate 37B against the engaging grooves 35D of the case portion 35A.

Here, the depth of the engaging grooves 35D in the case portion 35A is substantially equal to the total thickness of the opposed plate 37B and the peripheral edge portion of the diaphragm forming plate 37A. Thus, the diaphragm forming plate 37A is fixed while being held between the case portion 35A and the opposed plate 37B.

Figure 3A:
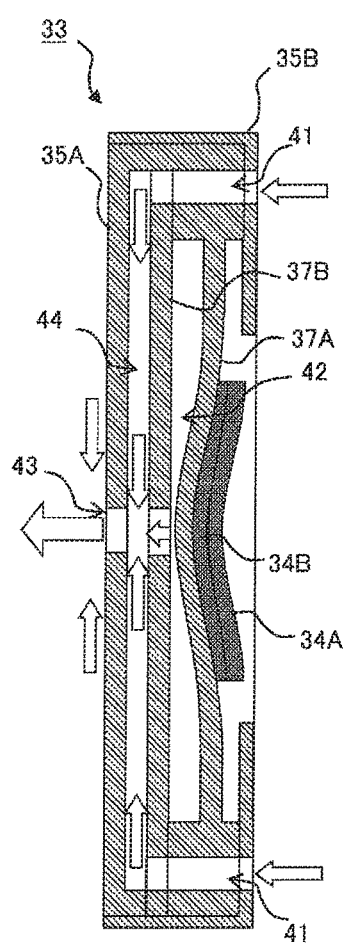
FIGS. 3A and 3B include operation views of the piezoelectric driving part in the suction device of the first embodiment.
Figure 3B:
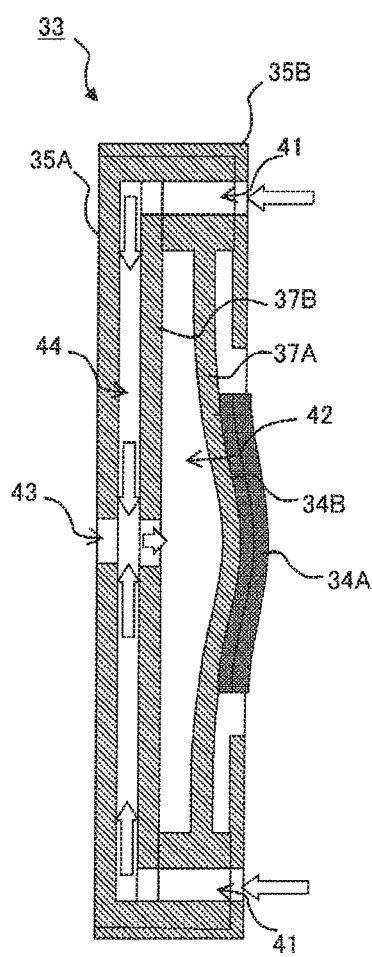

FIGS. 3A and 3B include cross-sectional views of the piezoelectric driving part 33.

Inside the piezoelectric driving part 33, a suction-side flow passage 41, a pump chamber 42, a discharge-side flow passage 43, and a connecting chamber 44 are provided.

The suction-side flow passage 41 is a space provided on an outer side of the outer peripheries of the diaphragm forming plate 37A and the opposed plate 37B inside the case portion 35A. The connecting chamber 44 is a space provided between the inner bottom surface of the case portion 35A and the opposed plate 37B inside the case portion 35A. The pump chamber 42 is a space provided between the diaphragm forming plate 37A and the opposed plate 37B inside the case portion 35A. The discharge-side flow passage 43 is a through hole provided in the inner bottom surface of the case portion 35A. The suction-side flow passage 41 and the discharge-side flow passage 43 communicate with each other with the connecting chamber 44 being disposed therebetween. The pump chamber 42 communicates with a position of the connecting chamber 44 with which the discharge-side flow passage 43 communicates so as to be opposed to the discharge-side flow passage 43.

In the piezoelectric driving part 33 having this structure, when an alternating-current driving voltage is applied to the piezoelectric element 34A, the piezoelectric element 34A attempts to expand and contract in the in-plane direction of the principal surface. However, since the piezoelectric element 34A is joined to the diaphragm 37 with the reinforcing plate 34B being disposed therebetween, it makes bending vibration in a concentric manner together with the reinforcing plate 34B and the diaphragm 37. Specifically, when the piezoelectric element 34A attempts to contract, the diaphragm 37 convexly bends toward the pump chamber 42 (rearward), as illustrated in FIG. 3A. Conversely, when the piezoelectric element 34A attempts to expand, the diaphragm 37 convexly bends toward the piezoelectric element 34A (frontward), as illustrated in FIG. 3B. In this way, the piezoelectric element 34A and the diaphragm 37 make bending vibration, and periodic volume variation and pressure variation correspondingly occur in the pump chamber 42.

When the volume of the pump chamber 42 decreases, the pump chamber 42 applies a positive pressure to the connecting chamber 44. Then, gas in the connecting chamber 44 is discharged outside through the discharge-side flow passage 43. When the volume of the pump chamber 42 increases, the pump chamber 42 applies a negative pressure to the connecting chamber 44. Then, the gas in the suction-side flow passage 41 is sucked into the connecting chamber 44. The gas in the suction-side flow passage 41 and an external gas are led into the gas discharged from the discharge-side flow passage 43 by the action of inertial force on the flow of gas produced in this way. Then, a flow of the gas from the suction-side flow passage 41 to the discharge-side flow passage 43 stationarily occurs in the piezoelectric driving part 33.

In the piezoelectric driving part 33 having the above-described structure, the diaphragm 37, the piezoelectric element 34A, and the reinforcing plate 34B corresponding to the moving part are entirely housed in a sealed interior (flow passages 2 and 28) of the flow-passage forming section 1. Hence, the driving sound and vibration caused in the piezoelectric driving part 33 are unlikely to leak outside from the flow-passage forming section 1. Further, since the filter 32 is provided in front of the piezoelectric driving part 33, the driving sound and vibration caused in the piezoelectric driving part 33 are unlikely to leak toward the front side of the flow-passage forming section 1. Still further, since the housing 4 is provided on the rear side of the piezoelectric driving part 33, the driving sound and vibration caused in the piezoelectric driving part 33 are unlikely to leak toward the rear side of the flow-passage forming section 1.

In the piezoelectric driving part 33, the members do not rub (slide) against one another, and this can make the caused driving sound and vibration less than in the motor-powered driving part of the related art. In the piezoelectric driving part 33, a member for closing the flow passage, such as a valve and a valve part, is not provided, and the suction-side flow passage 41 and the discharge-side flow passage 43 constantly communicate with each other. Therefore, the negative pressure in the flow passage 2 can be quickly released to the atmospheric pressure via the suction-side flow passage 41 and the discharge-side flow passage 43 of the piezoelectric driving part 33 only by stopping the piezoelectric driving part 33, and this can remove the adhesion of the nozzle 11 to the affected part. For this reason, the operation of opening the valve or the valve part is unnecessary, and the nozzle 11 easily separates from the skin. This rarely causes discomfort to the user. Further, a complicated mechanism, such as a valve or a valve part, is unnecessary, and this can improve the responsiveness when a negative pressure is generated and when the negative pressure is released.

Further, the piezoelectric driving part 33 is configured so that the total cross-sectional area of the discharge-side flow passage 43 opening on the rear side is less than the total cross-sectional area of the suction-side flow passage 41 opening on the front side. This structure can reduce the driving sound and vibration of the piezoelectric driving part 33 leaking outside from the piezoelectric driving part 33 through the discharge-side flow passage 43.

In this structure, the piezoelectric driving part 33 is configured so that fluid is sucked from the front side and the fluid is discharged to the rear side by making the flowing direction of the sucked gas and the flowing direction of the discharged gas substantially the same, as shown by dotted arrows in FIGS. 1A and 1B. With this structure, the path of the fluid can be made substantially linear and the path length of the piezoelectric driving part 33 on the rear side can be made extremely short (the path length is about zero) in the flow-passage forming section 1 that houses the piezoelectric driving part 33. Then, the pressure loss of the fluid occurring inside the flow-passage forming section 1 can be suppressed, the flow rate and flow velocity of the fluid sucked by the flow-passage forming section 1 can be increased, and the size of the flow-passage forming section 1 can be reduced. Further, since the path length of the fluid decreases on the front and rear sides of the piezoelectric driving part 33, buffers against the fluid can be reduced. Thus, it is possible to shorten the time required from when the piezoelectric driving part 33 starts driving to when the pressure of the fluid reaches a predetermined pressure and to improve the operation responsiveness of the suction device 9 and the flow-passage forming section 1.

The suction device 9 according to this embodiment can be configured as described above.

The power feeding circuit for feeding power to the driving unit 13 described in the embodiment may be provided integrally with the driving unit 13 without being provided inside the housing 4. When the power feeding circuit is integrally provided, the structures of the housing 4 and the like are omitted, and the configuration can be simplified further. The shapes of the nozzle 11 and the storage unit 14 are not limited to the cylindrical shape, and may be other shapes. For example, when the suction device 9 is used as a breast-milk suction device or a phlegm suction device, the nozzle 11 may be shaped like a funnel or a straw. The structure for separating the gas and the collection object (liquid) contained in the fluid in the flow passage 2 may be different from the above-described one. For example, the gas and the liquid contained in the fluid can be easily separated by dividing the flow passage 2 into a plurality of chambers and connecting the chambers or adopting a valve structure. The structure of the piezoelectric driving part 33 may be different from the above-described one. For example, the number of the discharge-side flow passages and the number of the suction-side flow passages provided in the piezoelectric driving part 33 and the paths thereof and the like can be changed appropriately. The portions of the piezoelectric driving part 33 except for the diaphragm 37, the diaphragm forming plate 37A, and the reinforcing plate 34B corresponding to the moving part may be appropriately provided integrally with the members that constitute the flow-passage forming section 1. When the portions are integrally provided, the noise can be even further reduced because the portions connected between the members are reduced in the whole suction device.

Figure 4:
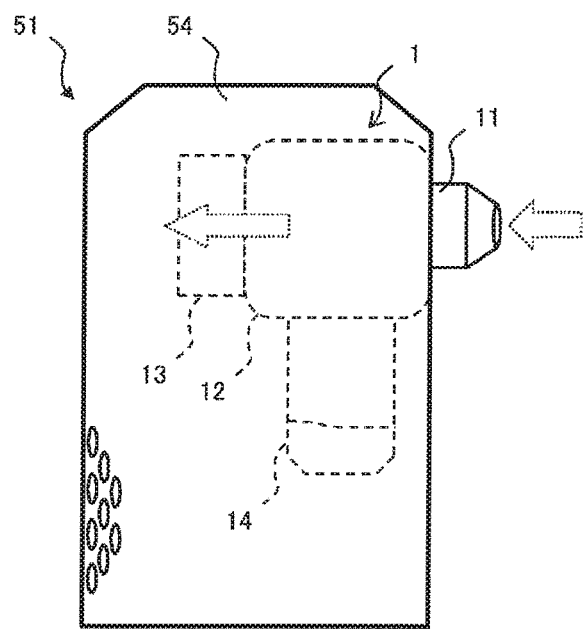
FIG. 4 is a side view of a suction device according to a second embodiment.

Next, a suction device according to a second embodiment of the present invention will be described. FIG. 4 is a side view of a suction device 51 according to the second embodiment.

While the suction device 51 has almost the same configuration as the configuration of the above-described first embodiment, it includes a housing 54 having a structure different from the structure in the above-described first embodiment. The housing 54 houses, among a nozzle 11, a separator 12, a driving unit 13, and a storage unit 14 that constitute a flow-passage forming section 1, the separator 12, the driving unit 13, and the storage unit 14. Only the nozzle 11 protrudes outside.

The present invention may be configured like the suction device 51. According to this configuration, the driving sound and vibration caused in the driving unit 13 and leaking to the separator 12 and the storage unit 14 can be unlikely to leak outside.

Figure 5:
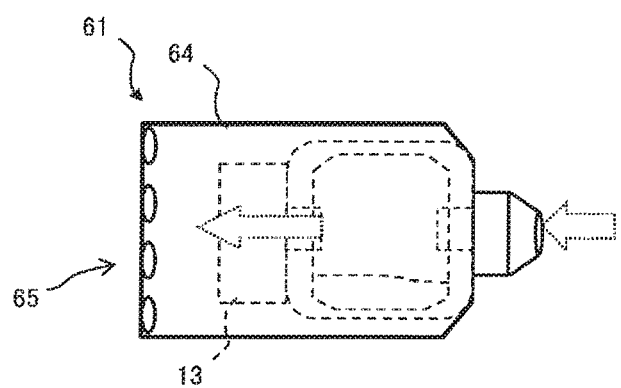
FIG. 5 is a side view of a suction device according to a third embodiment.

Next, a suction device according to a third embodiment of the present invention will be described. FIG. 5 is a side view of a suction device 61 according to the third embodiment.

While the suction device 61 has almost the same configuration as the configuration of the above-described first embodiment, it includes a housing 64 having a structure different from the structure in the above-described first embodiment. The housing 64 is shaped like a cylinder extending in the front-rear direction, and has air vents 65 at a position opposed to a rear side of a driving unit 13.

The present invention may be configured like the suction device 61. This configuration can reduce the size of the suction device 61 and can make the path of fluid linear as a whole. This can further suppress the pressure loss occurring in the path of the fluid.

Figure 6:
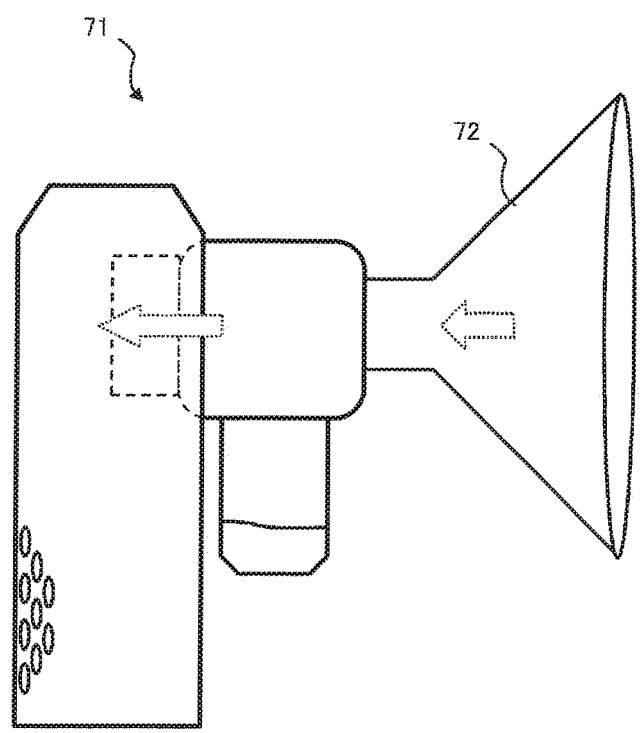
FIG. 6 is a side view of a suction device according to a fourth embodiment.

Next, a suction device according to a fourth embodiment of the present invention will be described. FIG. 6 is a side view of a suction device 71 according to the fourth embodiment.

While the suction device 71 has almost the same configuration as the configuration of the above-described first embodiment, it includes a nozzle 72 having a structure different from the structure in the above-described first embodiment. The suction device 71 is configured as a breast-milk suction device, and the nozzle 72 is shaped like a funnel to be fit the shape of breasts.

The present invention may be configured like the suction device 71. This can configure a compact and silent breast-milk suction device.

Next, fixing methods for the driving part in the suction device will be described.

Figure 7G:
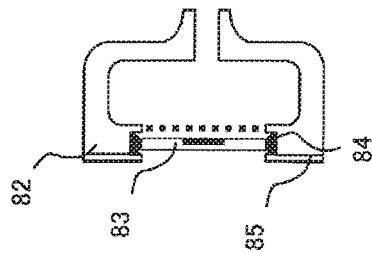
FIGS. 7A to 7G include cross-sectional views of the principal part, illustrating fixing methods for a driving part.
Figure 7E:
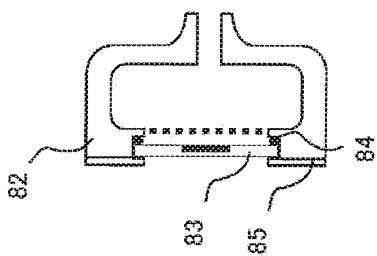
Figure 7F:
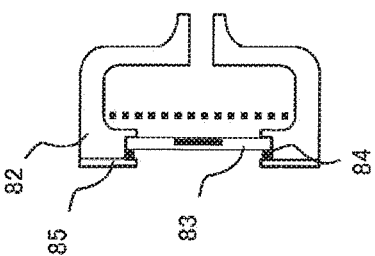
Figure 7C:
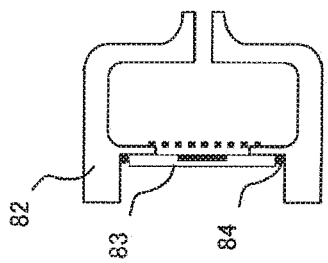
Figure 7D:
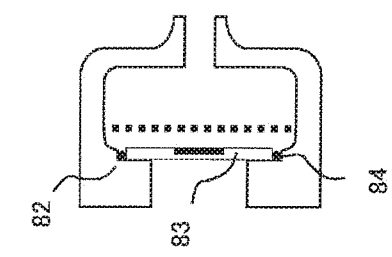
Figure 7A:
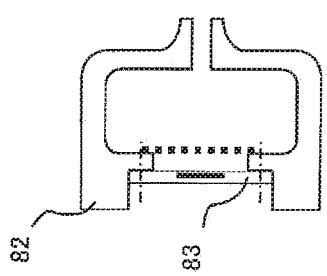
Figure 7B:
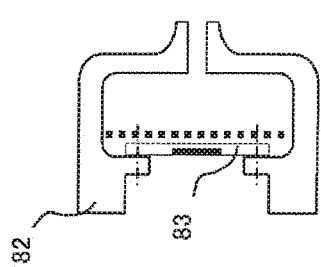

In FIGS. 7A and 7B, a flow-passage forming section 82 and a piezoelectric driving part 83 are fixed by screwing. When the flow-passage forming section 82 and the piezoelectric driving part 83 have high elasticity, they can be hermetically sealed only by screwing. However, a seal material is preferably provided on a contact surface between the flow-passage forming section 82 and the piezoelectric driving part 83. A suction-port side surface of the piezoelectric driving part 83 is in contact with the flow-passage forming section 82 in FIG. 7A, and a discharge-port side surface of the piezoelectric driving part 83 is in contact with the flow-passage forming section 82 in FIG. 7B. Since a flow of fluid occurs from the suction port side toward the discharge port side inside the flow-passage forming section 82, the flow-passage forming section 82 and the piezoelectric driving part 83 can be in closer contact with each other when the discharge-port side surface of the piezoelectric driving part 83 is in contact with the flow-passage forming section 82, as illustrated in FIG. 7B.

In FIGS. 7C and 7D, the flow-passage forming section 82 and the piezoelectric driving part 83 are fixed by fitting with an elastic member 84 located on an outer periphery being disposed therebetween. The elastic member 84 is, for example, an adhesive or a rubber packing material.

In FIGS. 7E and 7F, the flow-passage forming section 82 is provided with a lid member 85 to hold the piezoelectric driving part 83 from the suction port side and the discharge port side, and the flow-path forming section 82 and the piezoelectric driving part 83 are thereby fixed. In this case, it is also preferable to provide an elastic member 84.

In FIG. 7G, the flow-passage forming section 82 is provided with a piezoelectric lid member 85 to hold and fix an elastic member 84 from the suction port side and the discharge port side, and the driving part 83 is clamped by the elastic member 84 from the outer peripheral direction to fix the piezoelectric driving part 83.

By various methods described above, the flow-passage forming section and the piezoelectric driving part can be connected in a sealed state. The flow-passage forming section and the piezoelectric driving part may be fixed by other appropriate methods.

Figure 8A:
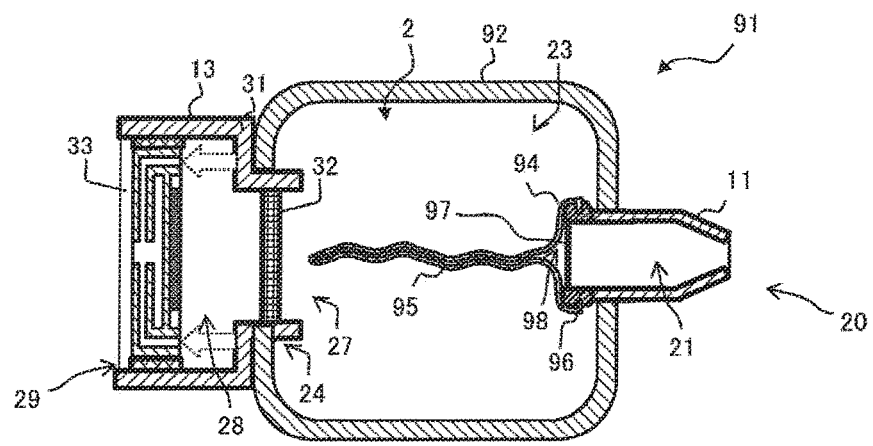
FIGS. 8A and 8B include sectional side views of a suction device according to a fifth embodiment.
Figure 8B:
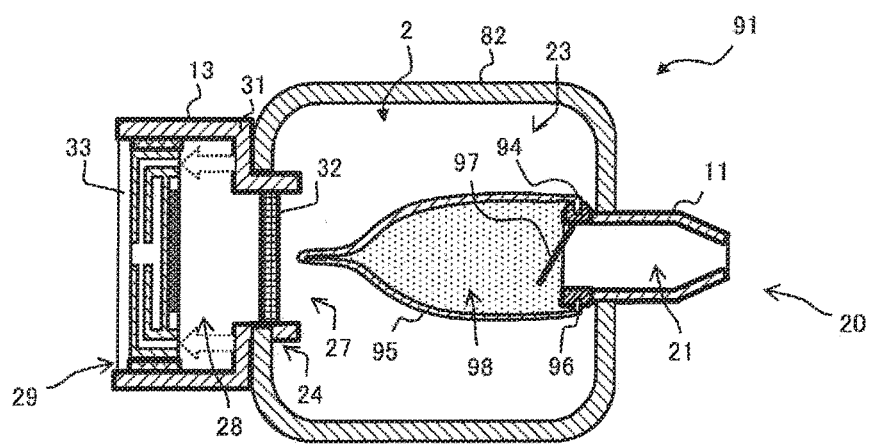

Next, a suction device according to a fifth embodiment of the present invention will be described. FIGS. 8A and 8B include side views of a suction device 91 according to the fifth embodiment.

While the suction device 91 has almost the same configuration as the configuration of the above-described first embodiment, it includes a flow-passage forming section 92 having a structure different from the structure in the above-described first embodiment. The flow-passage forming section 92 includes an inner canister 94 instead of the storage unit 14 provided in the first embodiment.

The inner canister 94 is roughly shaped like a bag, and is housed inside the flow-passage forming section 92 (flow passage 2). The inner canister 94 has an inner space 98 therein, and includes a bag mouth portion 96 and an expanding and contracting portion 95. The expanding and contracting portion 95 is a bag-shaped member formed of a resin material such as PET, and is expandable and contractable (herein plastically deformable). The expanding and contracting portion 95 may be formed of an elastic material, such as rubber, to be elastically deformable. The bag mouth portion 96 is an annular member attached at an aperture of the expanding and contracting portion 95, and is attached to a rear end portion of a nozzle 11 in a sealed state inside the flow-passage forming section 92 (flow passage 2). The bag mouth portion 96 is detachable from the rear end portion of the nozzle 11. The bag mouth portion 96 is provided with a check valve 97 that does not block the flow of the fluid flowing from the nozzle 11 into the expanding and contracting portion 95, but blocks the flow of the fluid flowing out from the expanding and contracting portion 95 into the nozzle 11.

Before use of the suction device 91, the inner canister 94 is in a contracted state in which the inner space 98 of the bag mouth portion 96 is crushed. When the suction device 91 is driven in such a state, a driving unit 13 discharges the air inside the flow passage 2 from a discharge port 29 to the outside. Thus, the pressure inside the flow passage 2 becomes a negative pressure, and the expanding and contracting portion 95 expands. Thus, the pressure in the inner space 98 of the expanding and contracting portion 95 also becomes a negative pressure, and the inner space 98 sucks an external fluid from the nozzle 11. When the inner canister 94 is completely expanded, the external fluid cannot be further sucked from the nozzle 11. Hence, the inner canister 94 is detached from the rear end portion of the nozzle 11, and is replaced with a new inner canister 94. This allows the external fluid to be sucked from the nozzle 11 again.

By providing the inner canister 94 inside the flow-passage forming section 92 as in the suction device 91, viscous liquid, such as nasal mucus, can be prevented from directly flowing into the flow passage 2, and the suction device 91 can be prevented from being put into an inoperable state by clogging of the flow passage and the like in the driving unit 13. Further, the sucked fluid can be taken out of the suction device 91 by replacing only the inner canister 94, and an operation of cleaning the flow-passage forming section 92 is unnecessary.

The present invention may be configured like the suction device 91. This can configure a more convenient suction device. The inner canister 94 may be separable from other portions that constitute the flow-passage forming section 92, or may be provided integrally with the other portions that constitute the flow-passage forming section 92. When the inner canister 94 is provided integrally with the flow-passage forming section 92, the noise can be even further reduced because portions connected between the members are reduced in the whole suction device.

Figure 9A:
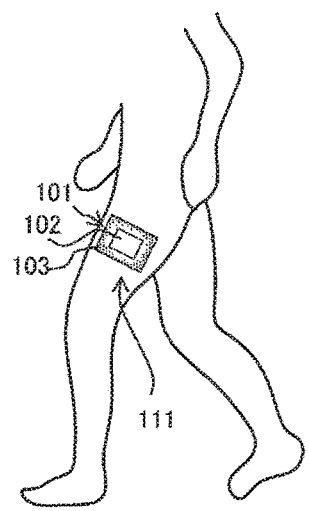
FIGS. 9A to 9C include schematic views illustrating a manner in which a suction device according to a sixth embodiment is used for a negative pressure wound therapy.

Next, a suction device according to a sixth embodiment of the present invention will be described. FIG. 9A is a schematic view illustrating a use mode of a suction device 101 according to the sixth embodiment.

The suction device 101 according to this embodiment is used for a negative pressure wound therapy. The negative pressure wound therapy is a therapy that promotes recovery of a wound site by keeping the wound site in a wet state with a wound dressing in a healing process of the wound site. The suction device 101 includes a suction unit 102 and a wound dressing 103. The wound dressing 103 is adhered around a wound site 111 of a patient who receives the negative pressure wound therapy in order to cover the wound site 111. The suction unit 102 is attached to a surface of the wound dressing 103, and applies a negative pressure around the wound site 111 covered with the wound dressing 103 in a sealed state to suck an exudate generated from the wound site 111.

Figure 9B:
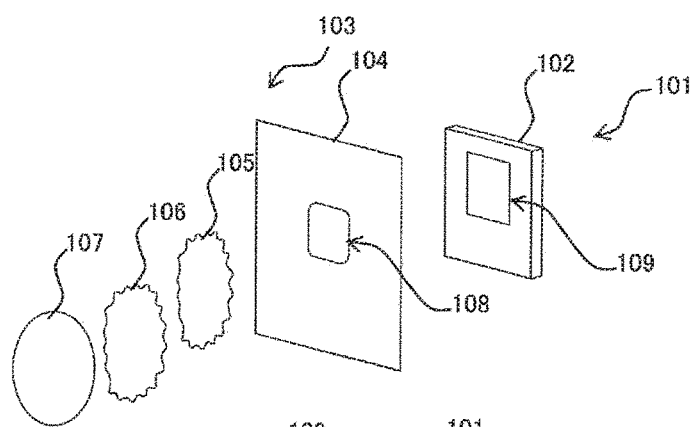
Figure 9C:
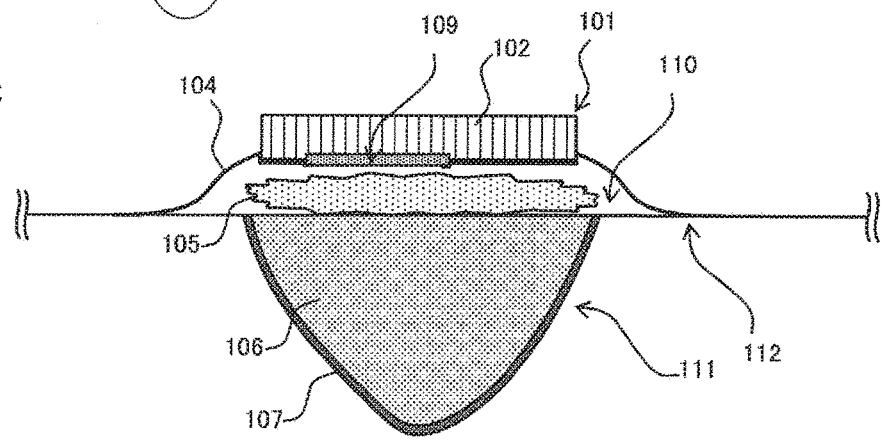

FIG. 9B is an exploded perspective view illustrating the outline structure of the suction device 101. FIG. 9C is a schematic view illustrating a worn state of the suction device 101 on the wound site.

The wound dressing 103 includes a protective film 104, an absorbing member 105, a covering member 106, and gauze 107. The gauze 107, the covering member 106, the absorbing member 105, and the protective film 104 are arranged in this order from a side of the wound site 111.

The gauze 107 is disposed in contact with a mucous membrane exposed in a wound interior of the wound site 111.

The covering member 106 is shaped to match the shape of the wound interior, and is then disposed on an upper side of the gauze 107 to fill the wound interior. The covering member 106 is formed of a porous material that transmits liquid. As the covering member 106, for example, polyurethane foam that is easily shaped to match the shape of the wound site can be used.

The absorbing member 105 is disposed on an upper side of the covering member 106. The absorbing member 105 absorbs liquid and holds the absorbed liquid. As the absorbing member 105, for example, cotton or a gel in which highly water-absorbing polymers are dispersed can be used.

The protective film 104 is a film that prevents the passage of liquid and gas, and has an aperture 108. An adhesive (not illustrated) for adhering to the skin is applied on a surface of the protective film 104 on the wound site side. The outer shape of the protective film 104 has an area larger than those of the absorbing member 105, the covering member 106, and the gauze 107 so as to cover the absorbing member 105, the covering member 106, and the gauze 107 entirely. The protective film 104 is adhered to a skin surface 112 around the wound site 111 with its outer peripheral portion exposed from the absorbing member 105, the covering member 106, and the gauze 107 being used as an adhesive surface. Thus, a closed space 110 is formed between the protective film 104 and the wound site 111.

The suction unit 102 has an outer shape like a thin box, and has a suction port 109 in a principal surface to be attached to the wound dressing 103. The suction unit 102 is attached to the wound dressing 103, for example, by an adhesive tape. The suction port 109 of the suction unit 102 is disposed as opposed to the aperture 108 of the protective film 104, and sucks the fluid (exudate) from the closed space 110 covered with the wound dressing 103.

Figure 10:
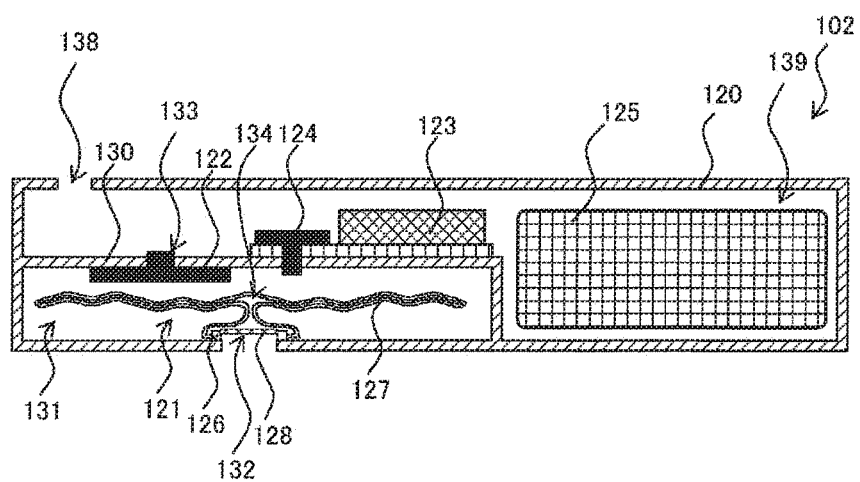
FIG. 10 is a cross-sectional view of the principal part of the suction device according to the sixth embodiment.
Figure 11B:
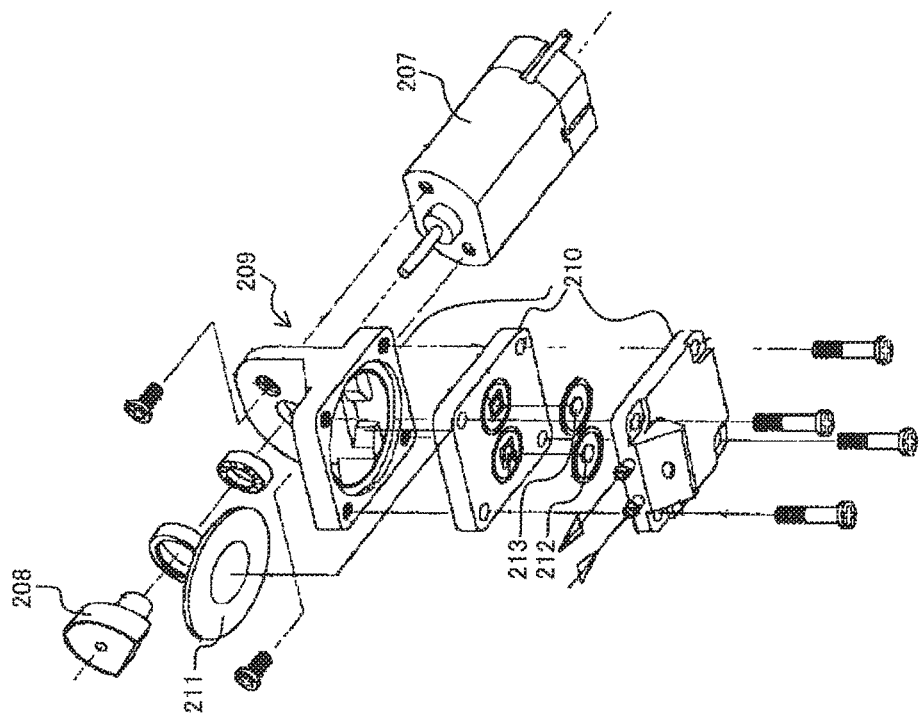
FIGS. 11A and 11B include explanatory views of a suction device of the related art.
Figure 11A:
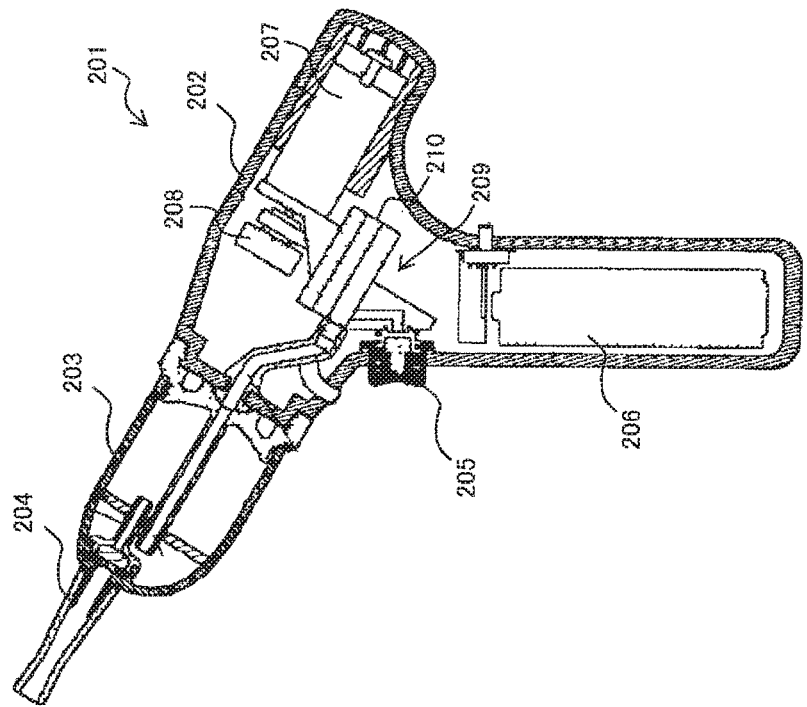

FIG. 10 is a cross-sectional view of the suction unit 102.

The suction unit 102 includes a flow-passage forming section 120, an inner canister 121, a piezoelectric driving part 122, a driving circuit 123, a pressure sensor 124, and a battery 125. The flow-passage forming section 120 has an inner partition 130. The inner partition 130 divides the internal space of the flow-passage forming section 120 into a flow passage 131 and a housing inner chamber 139. The flow-passage forming section 120 has an aperture at a position that does not face the housing inner chamber 139 but faces the flow passage 131, and the aperture forms a suction port 132 of the flow passage 131. The inner partition 130 also has an aperture, and the aperture forms a discharge port 133 of the flow passage 131. The flow passage 131 is sealed except at the suction port 132 and the discharge port 133. The flow-passage forming section 120 also has an air vent 138 at a position that does not face the flow passage 131 but faces the housing inner chamber 139. The air vent 138 allows the housing inner chamber 139 to communicate with the external space to make the pressure in the housing inner chamber 139 substantially equal to the outside pressure. The housing inner chamber 139 houses the driving circuit 123, the pressure sensor 124, and the battery 125.

The piezoelectric driving part 122 is attached at the discharge port 133 in the flow passage 131. The battery 125 supplies power to the piezoelectric driving part 122 and the pressure sensor 124 via the driving circuit 123. The pressure sensor 124 detects the air pressure in the flow passage 131. The driving circuit 123 controls the piezoelectric driving part 122 so that the air pressure in the flow passage 131 becomes constant.

The inner canister 121 is housed in the flow passage 131, and is attached at the suction port 132 of the flow passage 131. The inner canister 121 has an outline shape like a bag, has an internal space 134 therein, and includes a bag mouth portion 126 and an expanding and contracting portion 127. The expanding and contracting portion 127 is a bag-shaped member formed of a resin material such as PET, and is expandable and contractable (here, plastically deformable). The bag mouth portion 126 is an annular member attached at an aperture of the expanding and contracting portion 127, and is attached in a sealed state to the suction port 132 of the flow passage 131. The bag mouth portion 126 is detachable from the suction port 132. The bag mouth portion 126 is provided with a check valve 128 that does not block the flow of the fluid flowing from the suction port 132 into the expanding and contracting portion 127 but blocks the flow of the fluid flowing out from the expanding and contracting portion 127 to the suction port 132. In the internal space 134 of the inner canister 121, a fixing material for fixing an exudate, such as cotton or a gel in which highly water-absorbing polymers are dispersed may be provided.

Before the use of the suction unit 102, the inner canister 121 is in a contracted state in which the internal space 134 of the expanding and contracting portion 127 is crushed. When the suction unit 102 is driven in such a state, the piezoelectric driving part 122 discharges the air inside the flow passage 131 from the discharge port 133 to the housing inner chamber 139. Thus, the pressure inside the flow passage 131 becomes a negative pressure, and the expanding and contracting portion 127 attempts to expand. Thus, the pressure in the internal space 134 also becomes a negative pressure, and the external fluid is sucked from the suction port 132, that is, the exudate is sucked from the closed space 110 between the protective film 104 and the wound site 111. When the inner canister 121 is completely expanded, the exudate cannot be sucked further. Hence, the inner canister 121 is taken out from the inside of the flow-passage forming section 120 and is replaced with a new inner canister 121. This allows the exudate to be sucked from the closed space 110 between the protective film 104 and the wound site 111 again.

By providing the inner canister 121 as in the suction device 101, the exudate can be prevented from directly flowing into the flow passage 131, and the suction device 101 can be prevented from being put into an inoperable state by clogging of the flow passage and the like in the piezoelectric driving part 122. Further, the exudate can be taken out of the suction device 101 by replacing only the inner canister 121, and an operation of cleaning the flow passage 131 is unnecessary.

The present invention may be configured like the suction device 101. This configuration can make the suction device used for the negative pressure wound therapy highly convenient. While the suction unit 102 is directly attached to the wound dressing 103 in this embodiment, the wound dressing 103 and the suction unit 102 may be connected by a tube or the like and the suction unit 102 may be attached at a position far from the wound site 111. The inner canister 121 may be separable from other portions that constitute the flow-passage forming section 120, or may be provided integrally with the other portions that constitute the flow-passage forming section 120. When the inner canister 121 is provided integrally with the flow-passage forming section 120, the noise can be even further reduced because portions connected between the members are reduced in the whole suction device.

The present invention can be carried out by any configuration other than the above-described configurations as long as it corresponds to the configuration described in the claims.

While the suction device sucks a liquid which is a collection object in the embodiments of the present invention, the collection object may be a solid or gel substance other than the liquid. While the suction device sucks a gas serving as a fluid to be sucked together with the collection object in the embodiments of the present invention, the fluid to be sucked together with the collection object may be a liquid, such as water, or a colloid solution. In this case, a gel or a solid having a specific gravity higher than that of the fluid can be separated and stored as the collection object. The present invention is also applicable to, for example, a dust collection device for collecting minute dust and powder dust and a device for collecting an extra glue or adhesive applied to a workpiece. The configuration of the present invention is effective when these devices are used in a silent environment and when vibrations of these devices are suppressed.

1 flow-passage forming section
2 flow passage
4 housing
5 internal space
6 connecting port
7 air vent
9 suction device
11 nozzle
12 separator
13 driving unit
14 liquid container
20 suction port
21, 28 flow passage
22, 24, 25 aperture
23 upper chamber
26 lower chamber
27 internal suction port
29 discharge port
31 cylindrical body
32 filter
33 piezoelectric driving part
34A piezoelectric element
34B reinforcing plate
35A case portion
35B cover portion
37A diaphragm forming plate
37B opposed plate
41 suction-side flow passage
42 pump chamber
43 discharge-side flow passage
44 connecting chamber
91 suction device 92 flow-passage forming section
94 inner canister
95 expanding and contracting portion
96 bag mouth portion
101 suction device
102 suction unit
103 wound dressing
104 protective film
120 flow-passage forming section
121 inner canister
126 bag mouth portion
127 expanding and contracting portion

The invention claimed is:

1. A suction device comprising:
a flow-passage forming section having a suction port for sucking a fluid, a discharge port for discharging the fluid, and a flow passage through which the fluid flows, the flow passage extending from the suction port to the discharge port, and wherein the flow passage is sealed from an outside except at the suction port and the discharge port; and
a driving part for generating a flow of the fluid in the flow passage,
wherein the driving part comprises a moving part for transmitting a driving force to the fluid and the moving part is entirely disposed inside the flow-passage forming section,
wherein the moving part in a default non-moving state is radially contained within a case of the driving part and is coupled to the flow-passage forming section via the case, the case including a top portion coupled to a bottom portion, and the flow passage extending through each of the top portion and the bottom portion,
wherein the flow-passage forming section further includes a pump chamber having an inner capacity changed by a movement of the moving part in the flow-passage forming section, and
wherein the pump chamber constantly communicates with the flow passage and communicates with the outside via the flow passage.

2. The suction device according to claim 1, wherein the driving part is driven to make a fluid pressure in the flow passage on a side of the suction port a negative pressure relative to a fluid pressure outside the flow passage and to make a fluid pressure in the flow passage on a side of the discharge port a positive pressure relative to the fluid pressure outside the flow passage.

3. The suction device according to claim 2, wherein the moving part includes a piezoelectric member deformed by an application of a driving voltage and an elastic member having the piezoelectric member attached.

4. The suction device according to claim 2, wherein a total cross-sectional area of the flow passage on a discharge side is smaller than a total cross-sectional area of the flow passage on a suction side.

5. The suction device according to claim 1, wherein the moving part includes a piezoelectric member deformed by an application of a driving voltage and an elastic member having the piezoelectric member attached.

6. The suction device according to claim 5, wherein a reinforcing plate is fixed between the piezoelectric member and the elastic member to suppress a deformation of one of the piezoelectric member and the elastic member relative to the other of the piezoelectric member and the elastic member.

7. The suction device according to claim 1, wherein a total cross-sectional area of the flow passage on a discharge side is smaller than a total cross-sectional area of the flow passage on a suction side.

8. The suction device according to claim 1, wherein a flowing direction of the fluid sucked by the driving part is substantially the same as a flowing direction of the fluid discharged by the driving part.

9. The suction device according to claim 1, further comprising:
a filter for blocking a collection object contained in the fluid.

10. The suction device according to claim 1, further comprising:
a housing having an internal space housing a rear end portion of the flow-passage forming section with the discharge port wherein a front end portion of the flow-passage forming section with the suction port is exposed to an outside, and an air vent communicating with the internal space.

11. The suction device according to claim 1, wherein the flow-passage forming section further includes a storage unit provided on an upstream side of the driving part in the flow passage in a flow of the fluid to store a collection object contained in the fluid.

12. The suction device according to claim 11, further comprising:
a protective film having an aperture communicating with the suction port and provided to be adhered to a wound site.

13. The suction device according to claim 11, wherein the storage unit is a bag-shaped inner canister including a bag mouth portion communicating with the suction port and an expandable and contractable expanding and contracting portion having an internal space sealed except at the bag mouth portion, and wherein all flow discharged from the discharge port is first directed through the storage unit.

14. The suction device according to claim 13, wherein the bag mouth portion is detachable from the suction port.

15. The suction device according to claim 13, wherein the bag mouth portion connects the expanding and contracting portion and the suction port in a sealed state.

16. The suction device according to claim 13, wherein the expanding and contracting portion further includes a fixing material for fixing a liquid therein.

17. The suction device according to claim 1, wherein the pump chamber is in communication with the flow passage via an orifice into the pump chamber.

18. A suction device comprising:
an outer case including a flow-passage forming section having a suction port for sucking a fluid, a discharge port for discharging the fluid, and a flow passage through which the fluid flows, wherein the flow passage is sealed from an outside except at the suction port and the discharge port; and
a driving part for generating a flow of the fluid in the flow passage,
wherein the driving part comprises a moving part for transmitting a driving force to the fluid and the moving part is entirely disposed inside the flow-passage forming section,
wherein the driving part further comprises a support part to which the moving part is fixed, and
wherein the driving part includes a case having a top portion and a bottom portion, and side portions extending therebetween, the case radially enclosing each of the support part and the moving part therein, and the bottom portion supporting the support part against movement in at least one direction along the side portions relative to the outer case.

19. A suction device comprising:

a flow-passage forming section having a suction port for sucking a fluid, a discharge port for discharging the fluid, and a flow passage through which the fluid flows, the flow passage extending from the suction port to the discharge port, and wherein the flow passage is sealed from an outside except at the suction port and the discharge port; and a driving part for generating a flow of the fluid in the flow passage, wherein the driving part comprises a moving part for transmitting a driving force to the fluid and the moving part is entirely disposed inside the flow-passage forming section, wherein the moving part in a default non-moving state is retained within a case of the driving part and is coupled to the flow-passage forming section via the case, the case including a top portion and a bottom portion, with one of the top portion and the bottom portion being received in the other of the top portion and the bottom portion, and the flow passage extending through each of the top portion and the bottom portion, wherein the flow-passage forming section further includes a pump chamber having an inner capacity changed by a movement of the moving part in the flow-passage forming section, and wherein the pump chamber constantly communicates with the flow passage and communicates with the outside via the flow passage.

* * * * *